US012687646B2

(12) United States Patent
Maruyama

(10) Patent No.: US 12,687,646 B2
(45) Date of Patent: Jul. 21, 2026

(54) RADIATION DETECTION DEVICE COMPRISING A RADIATION DETECTOR, AN ELECTRICALLY-CONDUCTIVE BASE, A PROCESSING CIRCUIT, AND A PLURALITY OF RELAY BOARDS

(71) Applicant: Konica Minolta, Inc., Tokyo (JP)

(72) Inventor: Tadashi Maruyama, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 165 days.

(21) Appl. No.: 18/594,064

(22) Filed: Mar. 4, 2024

(65) Prior Publication Data

US 2024/0310536 A1     Sep. 19, 2024

(30) Foreign Application Priority Data

Mar. 14, 2023     (JP) ................................. 2023-039234

(51) Int. Cl.
*G01T 1/20*          (2006.01)
*A61B 6/42*          (2024.01)

(52) U.S. Cl.
CPC ........ *G01T 1/20184* (2020.05); *A61B 6/4283* (2013.01); *G01T 1/20* (2013.01); *G01T 1/20181* (2020.05); *G01T 1/20182* (2020.05)

(58) Field of Classification Search
CPC ....... A61B 6/42; A61B 6/4208; A61B 6/4233; A61B 6/4258; A61B 6/4266; A61B 6/4283; G01T 1/20; G01T 1/2006; G01T 1/2018; G01T 1/20182; G01T 1/20184; G01T 1/20186; G01T 1/20187; G01T 1/20188; G01T 1/24; G01T 1/241; G01T 1/243; G01T 1/244; G01T 1/247; G01T 1/248

USPC ..................................... 250/370.09; 378/98.8
See application file for complete search history.

(56) References Cited

U.S. PATENT DOCUMENTS

| | | | | |
|---|---|---|---|---|
| 6,658,082 B2 * | 12/2003 | Okumura | ................ | A61B 6/032 |
| | | | | 378/19 |
| 6,972,410 B2 * | 12/2005 | Takeda | .................. | H10F 39/189 |
| | | | | 250/370.09 |
| 7,136,452 B2 * | 11/2006 | Spartiotis | ............. | A61B 6/4233 |
| | | | | 378/19 |
| 7,442,939 B2 * | 10/2008 | Yagi | ........................ | G01T 1/247 |
| | | | | 250/370.11 |
| 7,989,772 B2 * | 8/2011 | Yagi | ....................... | G01T 1/2006 |
| | | | | 250/370.09 |
| 8,513,633 B2 * | 8/2013 | Koyanagi | ................. | G01T 1/16 |
| | | | | 250/584 |
| 8,581,202 B2 * | 11/2013 | Yamada | ............. | G01T 1/20188 |
| | | | | 250/370.09 |
| 10,341,581 B2 * | 7/2019 | Langley | .............. | G01T 1/20188 |

(Continued)

FOREIGN PATENT DOCUMENTS

JP          2012073186 A          4/2012

*Primary Examiner* — Allen C. Ho
(74) *Attorney, Agent, or Firm* — CANTOR COLBURN LLP

(57)                    ABSTRACT

A radiation detection device includes a radiation detector that detects radiation, an electrically-conductive base that supports the radiation detector, and a plurality of relay boards that relay electrical connection between the radiation detector and a processing circuit that processes a signal read out from the radiation detector. Each of grounds disposed on a respective one of the plurality of relay boards is electrically connected to the base.

7 Claims, 4 Drawing Sheets

(56)  References Cited

U.S. PATENT DOCUMENTS

| | | | |
|---|---|---|---|
| 11,852,756 B2 * | 12/2023 | Bogumil ............. | G01T 1/20188 |
| 12,111,430 B2 * | 10/2024 | Horiuchi ................ | A61B 6/488 |
| 12,169,261 B2 * | 12/2024 | Aida ................... | G01T 1/20184 |
| 12,207,955 B2 * | 1/2025 | Kawabata ................. | G01T 1/20 |
| 12,239,475 B2 * | 3/2025 | Shimizukawa ...... | A61B 6/4233 |
| 12,390,176 B2 * | 8/2025 | Yano .................... | A61B 6/4208 |

* cited by examiner

1

RADIATION DETECTION DEVICE COMPRISING A RADIATION DETECTOR, AN ELECTRICALLY-CONDUCTIVE BASE, A PROCESSING CIRCUIT, AND A PLURALITY OF RELAY BOARDS

CROSS REFERENCE TO RELATED APPLICATIONS

The present invention claims priority under 35 U.S.C. § 119 to Japanese Application No. 2023-039234, filed on Mar. 14, 2023, the entire contents of which being incorporated herein by reference.

BACKGROUND OF THE INVENTION

Technical Field

The present invention relates to a radiation detection device.

Description of Related Art

Conventionally, a radiation detection device which irradiates a target with radiation and detects the intensity distribution of the radiation transmitted through the target has been known and widely used in the medical field, the industrial field and the like. In recent years, a radiation detection device of a portable type (cassette type) allowed to be separated and carried from a photographing table has been developed and put into practical use. Such a radiation detection device has a panel shape and thus is often referred to as an FPD (Flat Panel Detector). The FPD internally includes a radiation detector which detects radiation.

The abovementioned portable-type radiation detection device is carried to a photographing position by a technician and thus is required to have small thickness and light weight. However, to implement reduction in the thickness and the weight, design made in consideration of the influence on an image caused by electrical noise attributed to small-thickness, high-density mounting is required.

Thus, there has been disclosed a configuration in which reducing electrical noise on an imaging detection panel (TFT) is enabled by covering the imaging detection panel by an electrically-conductive component and fixing the electrically-conductive component at a constant potential to cause the electrically-conductive component to function as a shield (for example, refer to JP 2012-73186A).

SUMMARY OF THE INVENTION

However, the configuration described in JP 2012-73186A is not a configuration in which readout circuits and drive circuits are disposed across a plurality of relay boards. Therefore, this configuration is not a configuration for which a consideration is given regarding the necessity to equalize reference potentials (R-GND) of the respective circuits each disposed on a respective one of the plurality of relay boards and make the reference potential of each circuit robust against the electrical noise.

Conventionally, as shown in FIG. 7, reference potentials G100 of the respective circuits (readout circuits 116 and drive circuits 117) each disposed on a respective one of a plurality of relay boards 114 are mutually connected via a control board 113 in which a processing circuit 1131 exists by using a wiring line W such as a flexible cable. Thus, impedance is high, and it is impossible to accurately keep the reference potentials G100 among the respective relay boards 114 at the same potential against electrical external noise and GND noise generated from the electrical circuit. There is a problem that image noise is generated if it is impossible to set the reference potentials G100 among the respective relay boards 114 to the same potential.

An object of the present invention is to provide a radiation detection device which can reduce image noise attributed to external electrical noise and internal electrical noise.

To achieve at least one of the abovementioned objects, according to an aspect of the present invention, a radiation detection device reflecting one aspect of the present invention includes:

a radiation detector that detects radiation, an electrically-conductive base that supports the radiation detector, and a plurality of relay boards that relay electrical connection between the radiation detector and a processing circuit that processes a signal read out from the radiation detector, wherein each of grounds disposed on a respective one of the plurality of relay boards is electrically connected to the base.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION

Hereinafter, one or more embodiments of the present invention will be described with reference to the drawings. However, the scope of the invention is not limited to the disclosed embodiments.

Figure 1:
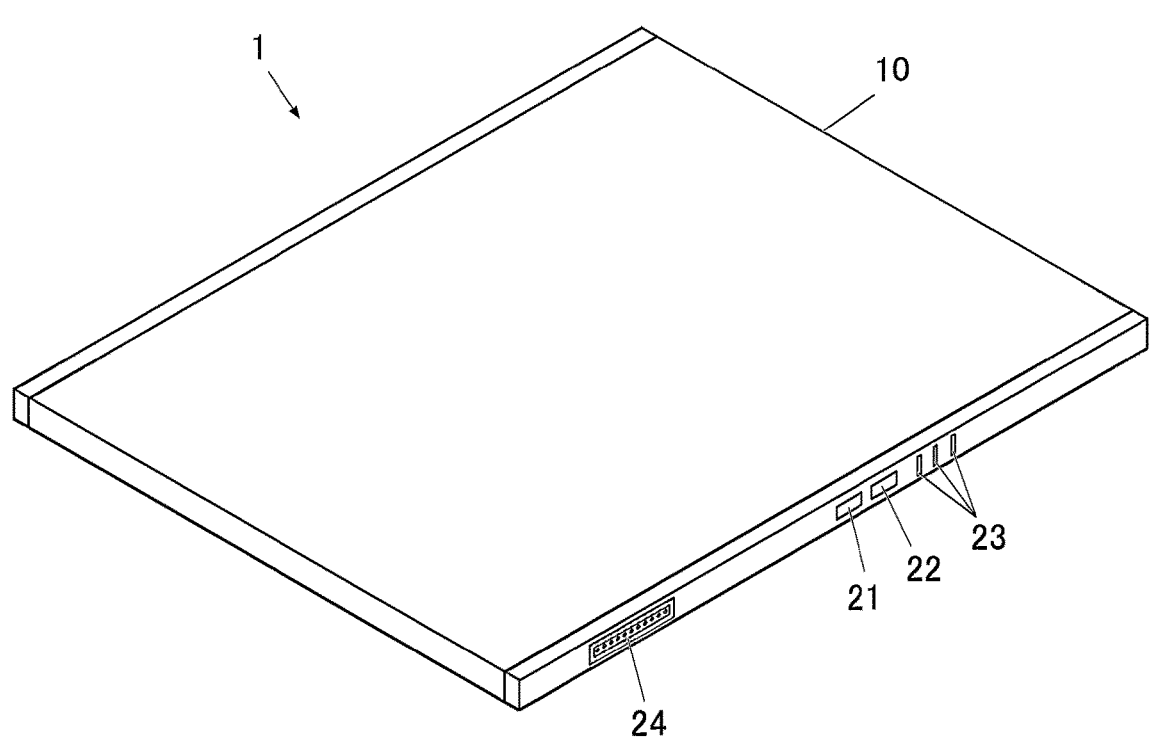
FIG. 1 is a perspective view showing the appearance of a radiation detection device according to the present embodiment.
Figure 2:
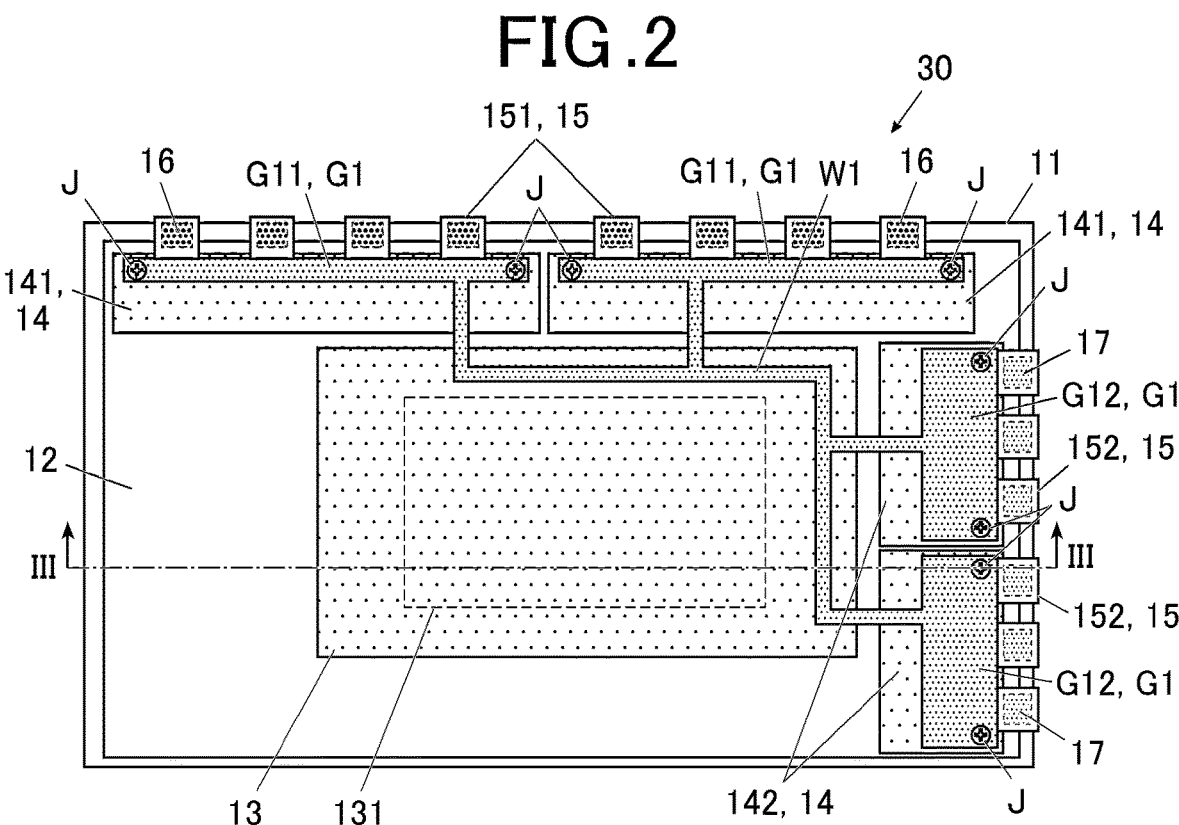
FIG. 2 is a plan view showing the configuration of an internal module.

As shown in FIG. 1, a radiation detection device 1 according to the present embodiment includes a casing 10. As shown in FIG. 2, the casing 10 houses an internal module 30 including a radiation detector 11, a base 12, a control board 13, a plurality of relay boards 14, a plurality of connecting circuit boards 15, a plurality of readout circuits 16, a plurality of drive circuits 17, and the like.

Furthermore, the radiation detection device 1 includes a power switch 21, an operation switch 22, a plurality of indicators 23, a connector 24 and the like in an outer side surface of the casing 10 (see FIG. 1).

The casing 10 is formed of a carbon fiber reinforced resin (CFRP) for example. The casing 10 is divisible into a box-shaped irradiation surface-side outer package having a front surface part which is a radiation irradiation surface and side surface parts and a back surface-side outer package as a lid body. The irradiation surface-side outer package and the back surface-side outer package are screwed together, for example, and can be easily separated. A waterproof component, such as a packing, which is not shown in the drawings, is disposed for the coupling part between the irradiation surface-side outer package and the back surface-side outer package so as to keep a liquid from entering the inside of the casing 10.

The radiation detector 11 is what is obtained by stacking and sealing a scintillator and TFTs (Thin Film Transistors) for example. The TFTs are flexible TFTs for example. The flexible TFTs are what are obtained by arranging a plurality of semiconductor elements and the TFTs which are switch elements on a matrix on an imaging surface of a substrate having flexibility. The imaging surface of the substrate is the surface on the side irradiated with radiation.

When the radiation detector 11 is irradiated with radiation, first, the scintillator emits light, the intensity of which depends on the intensity of the radiation. Next, the semiconductor elements (photodiodes) on the TFTs convert the light emitted by the scintillator to a charge and outputs the charge to the connecting circuit boards 15 as a signal.

The base 12 is a support substrate which supports the radiation detector 11 and boards such as the control board 13 and the plurality of relay boards 14. The base 12 is formed of an electrically-conductive component (for example Mg). The base 12 may be fixed to an inner surface of the casing 10 by an adhesive or agglutinant. The base 12 may be kept from moving through disposing a positioning component which is not shown in the drawings between the casing 10 and the base 12.

In the present embodiment, the potential of the base 12 is the same potential as the ground potential.

The control board 13 includes a processing circuit 131 including a CPU, a ROM, a RAM, a communication part and the like. The processing circuit 131 controls driving of the radiation detector 11 and processes a signal read out from the radiation detector 11. Specifically, the processing circuit 131 generates image data from the signal read out from the radiation detector 11 and outputs the image data to a console or the like which is not shown in the drawings.

The plurality of relay boards 14 are boards which relay electrical connection between the radiation detector 11 and the processing circuit 131. The plurality of relay boards 14 may directly connect the radiation detector 11 and the processing circuit 131 or may indirectly connect the radiation detector 11 and the processing circuit 131 with the interposition of another component.

Figures 3, 4:
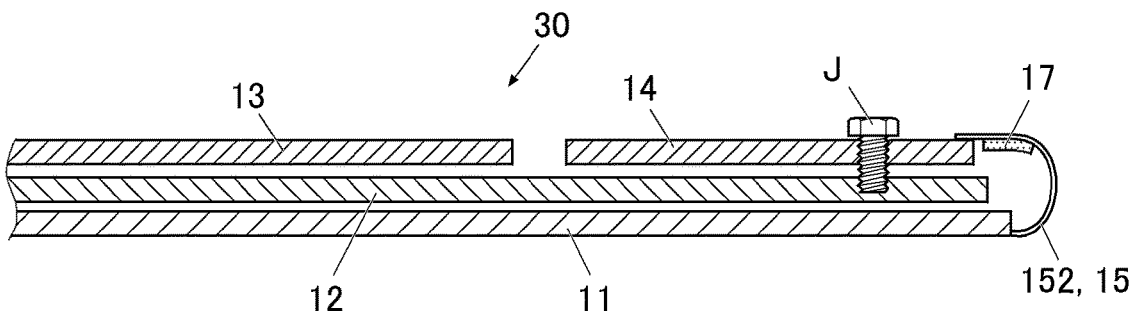
FIG. 3 is a sectional view along line III-III of the internal module of FIG. 2.
FIG. 4 is a plan view showing the configuration of the internal module in which other grounds (G-GND) different from grounds (R-GND) in an electrical system are disposed.

A ground (R-GND) G1 which is a potential (reference potential) serving as the basis of circuit operation is disposed on each of the plurality of relay boards 14. The grounds G1 disposed on the plurality of relay boards 14 are, for example, grounds G11 of the readout circuits 16 and grounds G12 of the drive circuits 17. As shown in FIG. 2 and FIG. 3, each ground G1 disposed on a respective one of the plurality of relay boards 14 is electrically connected to the base 12 by a plurality of (in FIG. 2, two) screws (connecting components) J. The number of screws J for electrically connecting each ground G1 to the base 12 may be one or three or more. However, it is more preferable to make the number of screws J larger because the impedance between connecting points can be reduced to a larger extent when the number of screws J is increased more. The "connecting points" refer to the points at which each of the grounds G1 is connected to the base 12 by a screw J.

In the present embodiment, the impedance between connecting points can be reduced by electrically connecting the reference potentials (grounds G1) to the electrically-conductive base 12 by using the screws J. Thus, the reference potentials can be stabilized.

As shown in FIG. 2, the respective grounds G1 each disposed on the respective one of the plurality of relay boards 14 are mutually connected via the control board 13 including the processing circuit 131 by using a wiring line W1 such as a flexible cable.

The connecting circuit boards (COF: Chip On Film) 15 are flexible boards and connect the radiation detector 11 and the relay board 14. The connecting circuit boards 15 include connecting circuit boards (S-COF) 151 on which the readout circuits 16 are disposed and connecting circuit boards (G-COF) 152 on which the drive circuits 17 are disposed.

The readout circuits (ROIC: Readout Integrated Circuit) 16 are circuits which read out a signal from the radiation detector 11.

The drive circuits (GDIC: Gate Driving Integrated Circuit) 17 are circuits which drive the radiation detector 11.

The grounds G11 of the readout circuits 16 are disposed on relay boards (SIF boards) 141 connected to the S-COFs 151. A plurality of (in FIG. 2, four) S-COFs 151 are connected to each SIF board 141.

The grounds G12 of the drive circuits 17 are disposed on relay boards (GIF boards) 142 connected to the G-COFs 152. A plurality of (in FIG. 2, three) G-COFs 152 are connected to each GIF board 142.

As shown in FIG. 4, other grounds (G-GND) G2 each different from the grounds (R-GND) G1 in the electrical system are each disposed on the respective one of the plurality of relay boards 14. The grounds G1 are reference potentials of an analog system circuit for example. The grounds G2 are reference potentials of a digital system circuit for example. By separating the grounds G1 and the grounds G2 as described above, mutual mixing of unintended noise can be suppressed. The grounds G1 and the grounds G2 are connected at one point at a place near a primary power supply.

The respective grounds G2 each disposed on the respective one of the plurality of relay boards 14 are mutually connected via the control board 13 including the processing circuit 131 by using a wiring line W2 such as a flexible cable.

As above, the radiation detection device 1 according to the present embodiment includes the radiation detector 11 that detects radiation, the electrically-conductive base 12 that supports the radiation detector 11, and the plurality of relay boards 14 that relay electrical connection between the radiation detector 11 and the processing circuit 131 that processes a signal read out from the radiation detector 11. Each of the grounds (R-GND) G1 disposed on the respective one of the plurality of relay boards 14 is electrically connected to the base 12.

Therefore, according to the radiation detection device 1 in accordance with the present embodiment, the distance between connecting points can be shortened compared with the connection using the conventional wiring line via the control board 113. Therefore, it becomes possible to reduce the impedance between the respective grounds G1 and the connection between the respective grounds G1 can be made firm. Thus, the respective grounds G1 can be set to the same potential accurately and stably. Accordingly, it becomes possible to suppress the influence due to electrical external noise and GND noise generated from the electrical circuit, so that image noise attributed to external electrical noise and internal electrical noise can be reduced.

Furthermore, according to the radiation detection device 1 in accordance with the present embodiment, the radiation detection device 1 includes the readout circuits 16 that read out a signal from the radiation detector 11 and the grounds G1 disposed on the plurality of relay boards 14 are the grounds G11 of the readout circuits 16.

Therefore, according to the radiation detection device 1 in accordance with the present embodiment, the connection between the grounds G11 of the respective readout circuits 16 can be made firm and the grounds G11 of the respective readout circuits 16 can be set to the same potential accurately and stably. Thus, image noise attributed to external electrical noise and internal electrical noise can be reduced.

Moreover, according to the radiation detection device 1 in accordance with the present embodiment, the radiation detection device 1 includes the drive circuits 17 that drive the radiation detector 11 and the grounds G1 disposed on the plurality of relay boards 14 are the grounds G12 of the drive circuits 17.

Therefore, according to the radiation detection device 1 in accordance with the present embodiment, the connection between the grounds G12 of the respective drive circuits 17 can be made firm and the grounds G12 of the respective drive circuits 17 can be set to the same potential accurately and stably. Thus, image noise attributed to external electrical noise and internal electrical noise can be reduced.

Furthermore, according to the radiation detection device 1 in accordance with the present embodiment, each of the grounds G1 disposed on the respective one of the plurality of relay boards 14 is electrically connected to the base 12 by the connecting components (screws J).

Therefore, according to the radiation detection device 1 in accordance with the present embodiment, the impedance between connecting points can be reduced and thus the respective grounds G1 can be set to the same potential accurately and stably.

Moreover, according to the radiation detection device 1 in accordance with the present embodiment, the radiation detection device 1 includes the connecting circuit boards 15 that connect the radiation detector 11 and the relay board 14 and the readout circuits 16 are disposed on the connecting circuit boards 15.

Therefore, according to the radiation detection device 1 in accordance with the present embodiment, a signal from the radiation detector 11 can be read out with a simple configuration and thus a radiation image can be generated without making the device configuration complicated.

Furthermore, according to the radiation detection device 1 in accordance with the present embodiment, the radiation detection device 1 includes the connecting circuit boards 15 that connect the radiation detector 11 and the relay board 14 and the drive circuits 17 are disposed on the connecting circuit boards 15.

Therefore, according to the radiation detection device 1 in accordance with the present embodiment, the radiation detector 11 can be driven with a simple configuration and thus the radiation detector 11 can be controlled without making the device configuration complicated.

Moreover, according to the radiation detection device 1 in accordance with the present embodiment, the other grounds (G-GND) G2 each different from the grounds (R-GND) G1 in the electrical system are each disposed on the respective one of the plurality of relay boards 14.

Therefore, according to the radiation detection device 1 in accordance with the present embodiment, by separating the grounds G1 and the grounds G2 different in the use purpose, mutual mixing of unintended noise can be suppressed and thus the respective grounds G1 and G2 can be stabilized.

Furthermore, according to the radiation detection device 1 in accordance with the present embodiment, the potential of the base 12 is the same potential as the ground potential.

Therefore, according to the radiation detection device 1 in accordance with the present embodiment, the potential of the base 12 can be stabilized and thus the respective grounds G1 connected through the base 12 can be stabilized.

Although specific description has been made above on the basis of the embodiment according to the present invention, the present invention is not limited to the abovementioned embodiment and can be changed without departing from the gist thereof.

For example, in the abovementioned embodiment, description has been made with exemplification of the configuration including the relay boards (SIF boards) 141 connected to the connecting circuit boards (S-COFs) 151 on which the readout circuits 16 are disposed and the relay boards (GIF boards) 142 connected to the connecting circuit boards (G-COFs) 152 on which the drive circuits 17 are disposed as the plurality of relay boards 14 that relay electrical connection between the radiation detector 11 and the processing circuit 131. However, the configuration is not limited thereto.

Figure 5:
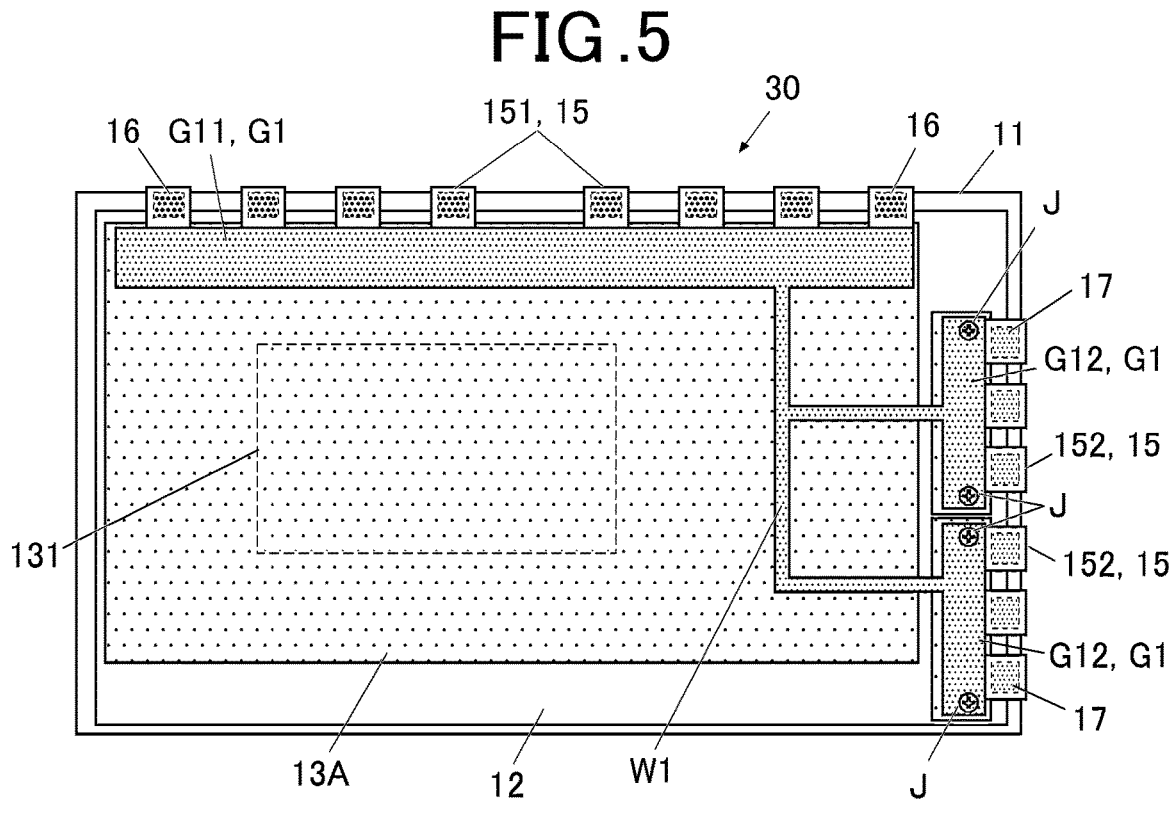
FIG. 5 is a plan view showing a modification example of the internal module in which SIF boards are formed as a board monolithic with a control board.

For example, as shown in FIG. 5, the SIF boards 141 may be formed as a board monolithic with a control board 13A including the processing circuit 131. In this case, the ground G11 of the readout circuits 16 is disposed on the control board 13A. The grounds G12 of the drive circuits 17 each disposed on a respective one of the GIF boards 142 are each electrically connected to the base 12 by a plurality of (in FIG. 5, two) screws J. Furthermore, the ground G11 of the readout circuits 16 disposed on the control board 13A and the grounds G12 of the drive circuits 17 each disposed on the respective one of the GIF boards 142 are mutually connected by using the wiring line W1 such as a flexible cable. The ground G11 of the readout circuits 16 disposed on the control board 13A may be electrically connected to the base 12 by a plurality of screws J.

Figure 6:
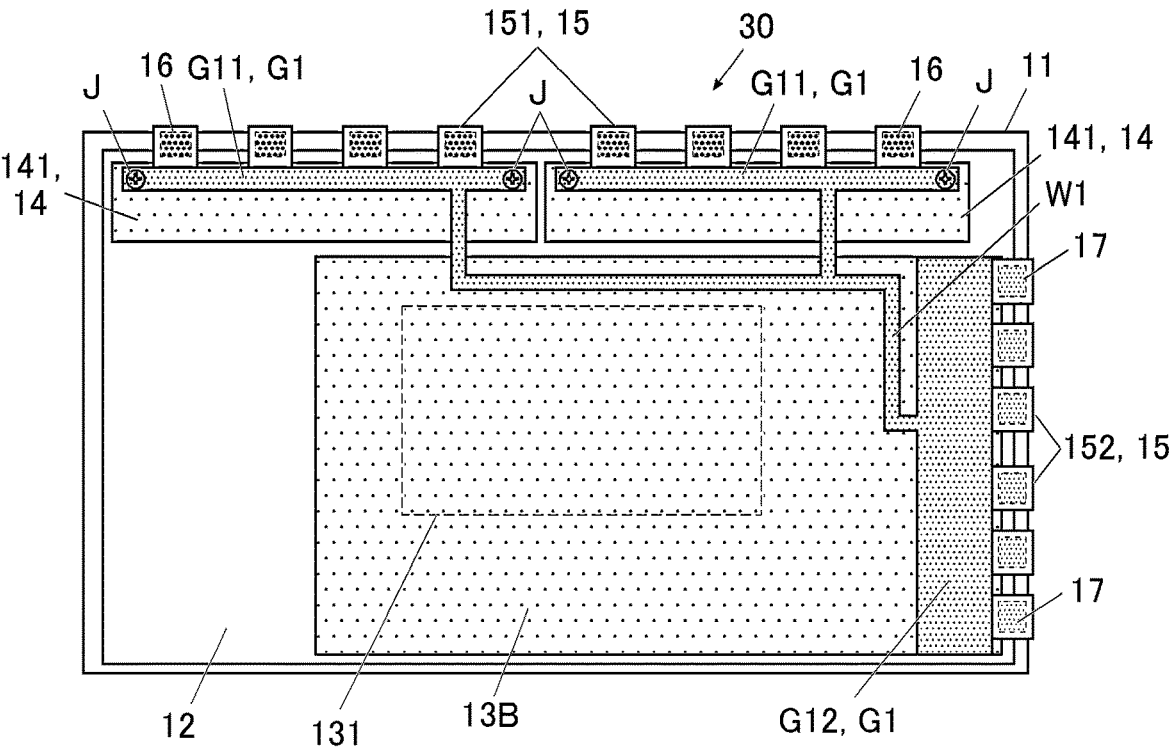
FIG. 6 is a plan view showing a modification example of the internal module in which GIF boards are formed as a board monolithic with the control board.
Figure 7:
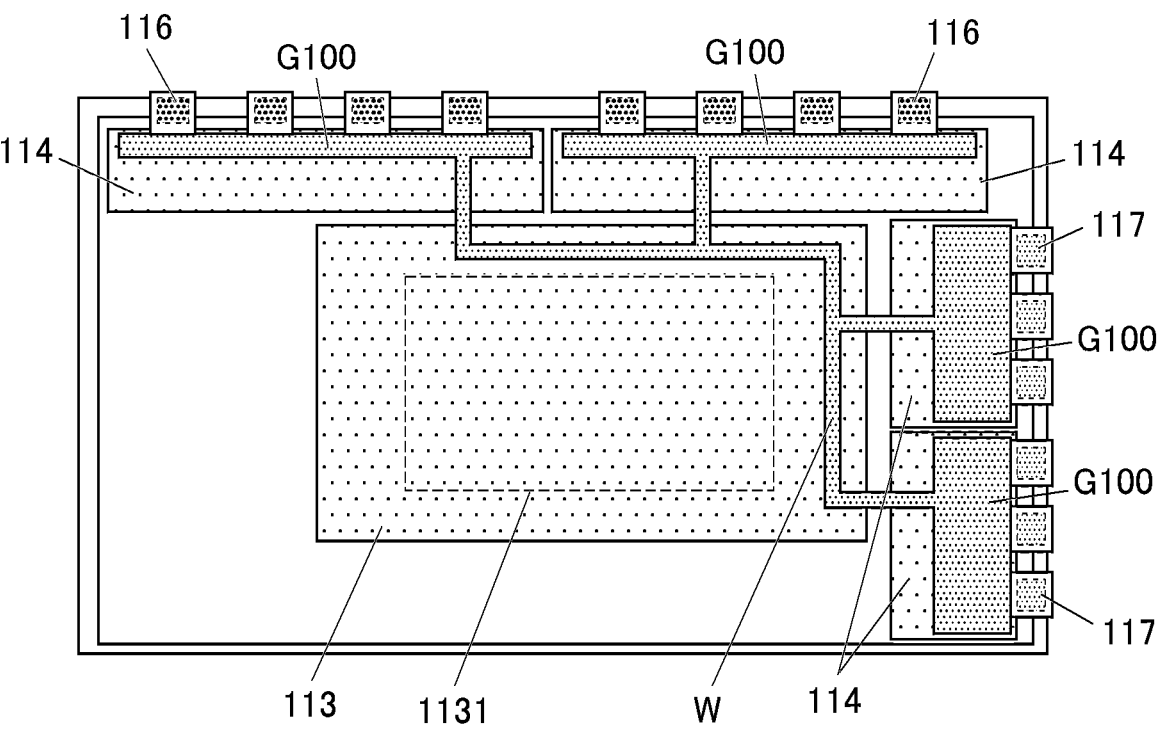
FIG. 7 is a plan view showing the configuration of an internal module of a radiation detection device according to a related art.

Moreover, as shown in FIG. 6, the GIF boards 142 may be formed as a board monolithic with a control board 13B including the processing circuit 131. In this case, the ground G12 of the drive circuits 17 is disposed on the control board 13B. The grounds G11 of the readout circuits 16 each disposed on a respective one of the SIF boards 141 are each electrically connected to the base 12 by a plurality of (in FIG. 6, two) screws J. Furthermore, the ground G12 of the drive circuits 17 disposed on the control board 13B and the grounds G11 of the readout circuits 16 each disposed on the respective one of the SIF boards 141 are mutually connected by using the wiring line W1 such as a flexible cable. The ground G12 of the drive circuits 17 disposed on the control board 13B may be electrically connected to the base 12 by a plurality of screws J.

Furthermore, in the abovementioned embodiment, each ground G1 disposed on the respective one of the plurality of relay boards 14 is electrically connected to the base 12 by the plurality of screws J. However, the configuration is not limited thereto. For example, the ground G1 may be connected by using a connecting component other than the screw J instead of being connected by the screw J. Alternatively, the relay board 14 and the base 12 may be directly connected by a method such as through-hole mounting.

Besides, also regarding detailed configurations and detailed operation of the respective devices forming the radiation detection device, changes can be made as appropriate without departing from the gist of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiation detection device, comprising:
a radiation detector that detects radiation;
an electrically-conductive base that supports the radiation detector;
a processing circuit; and
a plurality of relay boards that relay an electrical connection between the radiation detector and the processing circuit that processes a signal read out from the radiation detector,
wherein a ground disposed on a respective one of the plurality of relay boards is electrically connected to the electrically-conductive base.

2. The radiation detection device according to claim 1, further comprising:
a readout circuit that reads out the signal from the radiation detector,

wherein the ground disposed on the respective one of the plurality of relay boards is a ground of the readout circuit.

3. The radiation detection device according to claim 2, further comprising:
a connecting circuit board that connects the radiation detector and the plurality of relay boards,
wherein the readout circuit is disposed on the connecting circuit board.

4. The radiation detection device according to claim 1, further comprising:
a drive circuit that drives the radiation detector,
wherein the ground disposed on the respective one of the plurality of relay boards is a ground of the drive circuit.

5. The radiation detection device according to claim 4, further comprising:
a connecting circuit board that connects the radiation detector and the plurality of relay boards,
wherein the drive circuit is disposed on the connecting circuit board.

6. The radiation detection device according to claim 1, further comprising:
a connecting component,
wherein each of the grounds disposed on the respective one of the plurality of relay boards is electrically connected to the electrically-conductive base by the connecting component.

7. The radiation detection device according to claim 1, wherein another ground different from a ground in an electrical system are each disposed on the respective one of the plurality of relay boards.

* * * * *